United States Patent
Heinz et al.

(10) Patent No.: US 6,229,018 B1
(45) Date of Patent: May 8, 2001

(54) PROCESS FOR THE PREPARATION OF NICOTINIC ACID

(75) Inventors: Dieter Heinz, Leverkusen; Wolfgang Hölderich, Frankenthal; Steffen Krill, Speyer; Wolfgang Böck, Langenselbold; Klaus Huthmacher, Gelnhausen, all of (DE)

(73) Assignee: Degussa Aktiengesellschaft, Dusseldorf (DE)

( * ) Notice: Subject to any disclaimer, the term of this patent is extended or adjusted under 35 U.S.C. 154(b) by 0 days.

(21) Appl. No.: 09/386,951

(22) Filed: Aug. 31, 1999

(30) Foreign Application Priority Data

Sep. 1, 1998 (DE) ............................... 198 39 559

(51) Int. Cl.$^7$ ............................... C07D 213/803
(52) U.S. Cl. ............................... 546/320
(58) Field of Search ............................... 546/320

(56) References Cited

U.S. PATENT DOCUMENTS 3,803,156 * 4/1974 Ryoichi et al. .

FOREIGN PATENT DOCUMENTS 543510 12/1973 (CH) .
747259 12/1996 (EP) .

OTHER PUBLICATIONS

Jaras, et. al., "Preparation of Pyridinemonocarboxylic Acids by Catalytic Vapour Phse Oxidation of Alkylpyridines", J. appl. Chem. Biotechnol., 27, pp. 499–509, 1977.*

"Preparation of Pyridinemonocarboxylic Acids By Catalytic Vapour Phase Oxidation of Alsylpyridines", Jaeraes, et al., Journal of applied Chemistry & Biotechnology, 1977, XP000644583 pp. 499–509.

* cited by examiner

Primary Examiner—John Kight
Assistant Examiner—Binta Robinson
(74) Attorney, Agent, or Firm—Smith, Gambrell & Russell, LLP

(57) ABSTRACT

A process for the preparation of nicotinic acid by the direct oxidation of β-picoline in the gas phase, wherein water and β-picoline are fed separately to the catalyst bed and the catalyst is based on a titanium dioxide support which has been prepared by the sulfate method and has a high specific surface area and a vanadium oxide content of from 5 to 50 %.

11 Claims, No Drawings

PROCESS FOR THE PREPARATION OF NICOTINIC ACID

INTRODUCTION AND BACKGROUND

The present invention relates to a new and improved process for the preparation of nicotinic acid by the direct oxidation of β-picoline in the gas phase, wherein water and β-picoline are fed separately to the catalyst bed and the catalyst is based on a titanium dioxide support which has been prepared by the sulfate method and has a high specific surface area and a vanadium oxide content of from 5 to 50%.

Nicotinic acid is widely used in the fields of medicine and agriculture, both as a vitamin and as an intermediate for pharmaceuticals and plant growth regulators.

Various processes are known for the synthesis of nicotinic acid from β-picoline. One of those processes is liquid phase direct oxidation using $HNO_3$ and $H_2SO_4$ (U.S. Pat. No. 2,586,555, 1952) at temperatures of from 75 to 300° C. and with yields of from 66 to 77%. Disadvantages of those processes are the high salt production that results, as well as the production of large streams of waste water. A microbiological process for oxidizing β-picoline to nicotinic acid (EP 442430, 1995) achieves a yield of 50% after a reaction time of 16 hours, the unsatisfactory space-time yield and the costly separation of the biomass from the nicotinic acid making industrial application appear disadvantageous.

In the gas phase, the ammoxidation of β-picoline to 3-cyanopyridine with subsequent hydrolysis to nicotinic acid is known (USSR Inventor's Certificate No. 235764, 1969). A disadvantage of that process is that two process steps are required, and the nicotinic acid must additionally be separated from the product mixture by means of crystallization. A total nicotinic acid yield of from 86 to 88% is mentioned. Likewise in the gas phase, there are several investigations into the direct oxidation of β-picoline using vanadium oxide catalysts. The best results mentioned are nicotinic acid yields of from 82 to 86% with the addition of air and water and at temperatures of from 250 to 290° C. (EP 747 359, WO 95/20577, 1995). The advantages of the latter process variant are that auxiliary substances and solvents are not required, with the exception of the non-critical substances water and air for the addition of oxygen. However, the yields of nicotinic acid are still markedly less than 90%. Accordingly, that process is not sufficiently economical.

An object of the present invention was, therefore, further to improve the direct oxidation of β-picoline to nicotinic acid and to achieve yields of ≧90%, in order markedly to improve the economics of the process.

SUMMARY OF THE INVENTION

The above and other objects of the present invention can be achieved by a improved process for the preparation of nicotinic acid by the direct oxidation of β-picoline wherein the β-picoline is supplied to the reactor separately from the water and wherein the β-picoline is only brought together with the water at the beginning of the catalyst bed. It is a feature of the present invention to use a catalyst that contains vanadium oxide and whose support consists of a titanium dioxide prepared by the sulfate method and having a high surface area (>100 $m^2/g$), the vanadium oxide content being from 5 to 50 wt.%. Air is used as the source of oxygen, but it is also possible to use pure oxygen or a varying mixture of oxygen and nitrogen. The air is fed to the catalyst either together with the β-picoline, with the water, or separately. It is especially preferred to add $CO_2$ to the starting material feed, as a result of which the selectivity of the reaction can be increased further.

The yields are especially high (up to 95%) when the specific surface area of the titanium dioxide support is greater than 100 $m^2/g$, especially greater than 250 $m^2/g$, when the catalyst has a sulfate content greater than 0.1%, and when the vanadium oxide content is from 5 to 50%, especially from 10 to 30%. The titanium dioxide is advantageously present mainly in the anatase form.

DETAILED DESCRIPTION OF INVENTION

In the industrial preparation of titanium dioxides, two processes are distinguished, the chloride process and the sulfate process (Ullmann's Encyklopädie der technischen Chemie, 4th edition, VCH Weinheim, Volume 18, p. 569). The chloride process consists of the steps of chlorination, cooling, $TiCl_4$ purification, $TiCl_4$ combustion and $TiO_2$ separation. The sulfate process consists of dissolving the titanium raw material in concentrated sulfuric acid and subsequently precipitating the titanium dioxide. In detail, that process consists of the steps of decomposition, dissolution and reduction, clarification, crystallization and hydrolysis. Both processes are followed by recovery processes in order to obtain a product that is as pure as possible. A characteristic feature of the sulfate process is above all the slight residual sulfate content in the titanium dioxide, which can be reduced but not completely avoided by washing. Varying chemical properties are also associated therewith (G. A. Zenkovets, A. M. Volodin, A. F. Bedilo, E. F. Burgina, E. M. Al'kaeva, Kinetics and Catalysis, Vol. 38 (1997) p. 669).

The direct oxidation according to the present invention of β-picoline to nicotinic acid is carried out at a reaction temperature of from 150 to 450° C., preferably from 200 to 325° C. and especially from 240 to 290° C., in a fixed bed reactor; alternatively, procedures in a fluidized bed, in a moving bed and, in the liquid phase, in a fixed bed, and a multiphase procedure in a trickle bed or autoclave, are also possible.

In order to achieve good results, the molar water/β-picoline ratio is to be from 15 to 100, especially from 25 to 75, and the molar oxygen/β-picoline ratio is to be from 5 to 40, especially from 10 to 35, and the catalyst load is to be at a WHSV (weight hourly space velocity=$[h^{-1}]$) of from 0.02 to 5 $h^{-1}$, especially from 0.04 to 1 $h^{-1}$ and more especially from 0.05 to 0.5 $h^{-1}$.

On account of the high yields and the ready separability of the nicotinic acid from the remaining product mixture (sublimation temperature of the nicotinic acid=235° C.), the synthesized product can be separated off at from 100 to 230° C. with a high degree of purity, and the water, the gas portions (predominantly oxygen and nitrogen), the pyridine-3-carbaldehyde intermediate and unreacted β-picoline can be recycled in gaseous form and brought together with fresh β-picoline and oxygen at the beginning of the catalyst bed. The $CO_2$ formed as the principal by-product by total oxidation can also be fed back, since it has been possible to establish that the addition of an additional feed gas stream or in the regas stream, which contains, for example, $N_2$, Ar, CO, $CH_4$, $N_2O$ and, especially, $CO_2$, can markedly increase the yield of the reaction, which falls at higher loads.

The support materials used are various commercially obtainable titanium dioxides, which have been prepared both by the chloride method and by the sulfate method. Titanium dioxides prepared by other precipitation processes can also be used. They differ in their specific surface area, which was determined by $N_2$ sorption and BET evaluation, as well as in their sulfate content.

The support materials were loaded directly with vanadium oxide by the following method:

A water-soluble vanadium compound is chosen as the vanadium precursor; there are generally used ammonium meta-vanadate, vanadium acetylacetonate or vanadium oxalate. According to the desired $V_2O_5$ load, the amount of vanadium precursor required therefor is converted into an aqueous solution. The titanium dioxide support material is added to that aqueous solution and the mixture is stirred. After an evaporation step, in which the water is separated off, there is obtained, with adequate intermixing, a solid consisting of the titanium dioxide and the vanadium precursor adsorbed thereon. The powdered product can then be conditioned by tempering in the usual way, as a result of which the desired $V_2O_5/TiO_2$ catalyst is obtained.

The process according to the invention is further illustrated by the Examples which follow.

The following titanium dioxides were used as support materials:

TABLE 1

Support materials

| Titanium dioxide (manufacturer) | BET surface area (m²/g) | Main crystal formation | Sulfate content |
|---|---|---|---|
| TiO₂-P25 (Degussa) | 50 | anatase | 0 |
| Hombitec K01 (Sachtleben Chemie) | 129 | anatase | 0.5% |
| Hombitec K03 (Sachtleben Chemie) | 130 | anatase | 1.5% |
| Hombifine N (Sachtleben Chemie) | 275 | anatase | 0.5% |
| Hombifine N* (Sachtleben Chemie) | 260 | anatase | 1.5% |

From the support materials according to Table 1, the $V_2O_5$—$TiO_2$ catalysts listed in Table 2 were prepared by the impregnation technique described below.

Ammonium meta-vanadate was used as the vanadium precursor in all cases. According to the desired load indicated, the amount of ammonium meta-vanadate required therefor was dissolved in distilled water. For the purpose of better solubility of the solid, the water was heated to approximately 40° C. The desired amount of titanium dioxide is added to that aqueous solution, and stirring is carried out. The water is removed in a rotary evaporator with continuous stirring and under a water-jet vacuum at an oil bath temperature of 100° C. The powdered product is then calcined at 450° C. for 4 hours and compressed to form tablets having a diameter of approximately 13 mm. From those tablets, the 1–1.6 mm split fraction is then sieved out in a comminution procedure and is used as the catalyst.

| Catalyst | Support | BET surface area (m²/g) | V₂O₅ content (desired) | V₂O₅ content (actual) |
|---|---|---|---|---|
| A | TiO₂-P25 | 25 | 2.5 | 2.3 |
| B | Hombitec K01 | 65 | 18 | 17 |
| C | Hombitec K03 | 61 | 18 | 12 |

-continued

| Catalyst | Support | BET surface area (m²/g) | V₂O₅ content (desired) | V₂O₅ content (actual) |
|---|---|---|---|---|
| D | Hombifine N | 40 | 20 | 19 |
| E | Hombifine N* | 35 | 20 | 20 |

EXAMPLE 1 (Comparison Example)

The reactor used is a tubular helix reactor made of steel, which is maintained at reaction temperature in an air—circulating oven. 3 g of catalyst A are introduced into the reactor. Air is used as the source of oxygen. Water and β-picoline are used in the form of a mixture and are pumped to the reactor together, where they are vaporized with the air and fed to the catalyst. At a reaction temperature of 265° C., a WHSV of 0.06 g/h of β-picoline/g of catalyst (=0.06 h⁻¹) and a molar ratio $O_2/H_2O/β$-picoline=40/100/1, a β-picoline conversion of 61.6% was measured with a nicotinic acid selectivity of 22% (molar)

EXAMPLE 2 (Comparison Example)

The same test arrangement as in Example 1 was repeated without catalyst. At a temperature of 275° C., an $O_2/H_2O/β$-picoline ratio of 40/70/1 (molar) and a feed amount ($H_2O+β$-picoline)=4.4 g/h, a β-picoline conversion of 30% to gaseous decomposition products was measured.

EXAMPLE 3 (Comparison Example)

The test of Example 2 was repeated, but this time no water was added. At a temperature of 275° C., an $O_2/β$-picoline ratio of 40/1 and a mass flow rate of β-picoline=0.325 g/h, a β-picoline loss of only 10% was measured.

EXAMPLE 4 (Comparison Example)

The construction of the test arrangement described in Example 1 was changed so that the air was enriched with β-picoline in a temperature-controlled saturator, while the water was heated separately and fed directly to the catalyst bed and only brought together with the air/β-picoline mixture there. Catalyst A (8.91 g) was used again. At a reaction temperature of 265° C., a WHSV of 0.05 h⁻¹ and an $O_2/H_2O/β$-picoline ratio of 40/70/1, a conversion of 59.9% and a nicotinic acid selectivity of 53.4% were achieved. The improvement as compared with the result of Example 1 confirms that, as observed in the comparison examples, the β-picoline decomposes in the presence of the water—independently of the catalyst.

EXAMPLES 5–14

In the further Examples according to the invention, therefore, the air/β-picoline mixture is always fed to the beginning of the catalyst bed separately from the water. Example 13 shows that smaller excesses of water and air and a high load (WHSV) lead to lower yields, which can be improved by the addition of $CO_2$ (Example 14).

Further variations and modifications of the foregoing will be apparent to those skilled in the art and are intended to be encompassed by the claims appended hereto.

German priority application 198 39 559.0 filed Sep. 1, 1998 is relied on and incorporated herein by reference.

Examples 5–14

| No. | Catalyst | T [° C.] | $O_2/H_2O/$ β-picoline (molar) | $CO_2$/β-picoline (molar) | WHSV [$h^{-1}$] | $m_{catalyst}$ [g] | Conversion [%] | Selectivity [mol-%] |
|---|---|---|---|---|---|---|---|---|
| 5 | D | 275 | 35/60/1 | — | 0.04 | 6.5 | 97 | 98 |
| 6 | D | 265 | 35/70/1 | — | 0.04 | 6.5 | 98 | 986 |
| 7 | D | 290 | 35/60/1 | — | 0.045 | 6.5 | 100 | 49 |
| 8 | E | 265 | 40/70/1 | — | 0.04 | 6.5 | 96 | 96 |
| 9 | B | 265 | 35/60/1 | — | 0.846 | 6.1 | 100 | 84 |
| 10 | C | 265 | 35/55/1 | — | 0.044 | 7.1 | 99 | 75 |
| 11 | D | 275 | 30/60/1 | — | 0.025 | 6.5 | 100 | 62 |
| 12 | D | 275 | 25/56/1 | — | 0.085 | 6.5 | 97 | 75 |
| 13 | D | 275 | 22/50/1 | — | 0.11 | 3.9 | 96 | 63 |
| 14 | D | 275 | 22/50/1 | 9/1 | 0.11 |  | 93 | 72 |

We claim:

1. A process for the preparation of nicotinic acid by the direct oxidation of β-picoline in the presence of water and in a catalyst bed comprising supplying β-picoline to a reactor separately from supplying the water to the reactor, bringing the β-picoline into contact with the water only at the beginning of the catalyst bed, said catalyst bed being filled with a $V_2O_5$-containing $TiO_2$-supported catalyst, said $TiO_2$-support (anatase) having been prepared by the surface method wherein titanium raw material is dissolved in concentrated sulfuric acid and titanium dioxide is subsequently precipitated, said $TiO_2$-support having a specific surface area greater than 100 $m^2$/g and a sulfate content greater than 0.1%.

2. The process according to claim 1 wherein the anatase has a specific surface area greater than 250 $m^2$/g.

3. The process according to claim 1, wherein the catalyst contains vanadium oxide content in an amount of from 5 to 50%.

4. The process according to claim 1, wherein the oxidation is carried out at a reaction temperature of 150 to 450° C.

5. The process according to claim 1, further comprising reacting the β-picoline with oxygen in an oxygen/β-picoline ratio of 5/1 to 40/1, and adding water in a β-picoline ratio water ratio of 15/1 to 100/1.

6. The process according to claim 1, further comprising reacting the β-picoline with oxygen in an oxygen/β-picoline ratio of 10/1 to 35/1, and adding water in a β-picoline ratio water ratio of 25/1 to 75/1.

7. The process according to claim 1, further comprising carrying out the oxidation at a WHSV (weight hourly space velocity) of 0.02 to 5 $h^{-1}$.

8. The process according to claim 1, further comprising carrying out the oxidation in a gas phase or in a liquid phase in a fixed bed reactor, a fluidized bed reactor or a moving bed reactor.

9. The process according to claim 1, further comprising carrying out the oxidation in a multiphase procedure, in a trickle bed reactor or autoclave.

10. The process according to claim 1, further comprising adding $CO_2$ to the oxidation to bring about an additional improvement in the nicotinic acid yield.

11. The process according to claim 1, further comprising at high yields of ≧90%, as a result of ready separability of the nicotinic acid, which sublimates at approximately 235° C., feeding back residual process gas to the catalyst bed and supplying to the catalyst bed fresh β-picoline and oxygen.

* * * * *